United States Patent
Gehrer et al.

[11] Patent Number: 5,939,595
[45] Date of Patent: *Aug. 17, 1999

[54] PREPARATION OF DIARYLETHANES

[75] Inventors: Eugen Gehrer, Ludwigshafen; Klemens Massonne, Westheim; Hermann Gausepohl, Mutterstadt; Martin Fischer, Ludwigshafen; Christopher William Rieker, Mannheim; Lorenz Siggel, Heidelberg, all of Germany

[73] Assignee: BASF Aktiengesellschaft, Ludwigshafen, Germany

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/639,833

[22] Filed: Apr. 26, 1996

[30] Foreign Application Priority Data

May 6, 1995 [DE] Germany .................. 195 16 717

[51] Int. Cl.⁶ .................. C07C 15/12; C07C 15/16; C07C 2/08; C07C 2/12
[52] U.S. Cl. .................. 585/25; 585/20; 585/21; 585/23; 585/24; 585/422; 585/426
[58] Field of Search .................. 585/20, 21, 23, 585/24, 25, 422, 426

[56] References Cited

U.S. PATENT DOCUMENTS

| | | | |
|---|---|---|---|
| 4,347,169 | 8/1982 | Sato et al. | 252/567 |
| 4,442,027 | 4/1984 | Sato et al. | 252/574 |
| 4,493,943 | 1/1985 | Sato et al. | 585/11 |
| 5,068,482 | 11/1991 | Akatsu et al. | 585/429 |
| 5,453,555 | 9/1995 | Chang et al. | 585/469 |

FOREIGN PATENT DOCUMENTS

| | | |
|---|---|---|
| A-15758 | 9/1980 | European Pat. Off. . |
| 0 421 340 | 4/1991 | European Pat. Off. . |
| A-1281757 | 5/1962 | France . |
| A-3118336 | 5/1991 | Japan . |

OTHER PUBLICATIONS

Hasegawa & Higashimura, "Selective Alkylation of Aromatic Hydrocarbons with Styrene by Solid Polymeric Oxo Acids.", Polymer Journal, vol. 12, No. 6, p. 407 (1980) No Month Available.

*Primary Examiner*—Elizabeth D. Wood
*Attorney, Agent, or Firm*—John H. Shurtleff

[57] ABSTRACT

A process for preparing diarylethanes of the general formula I

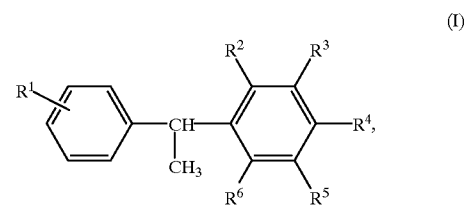

(I)

where $R^1$, $R^2$, $R^3$, $R^4$, $R^5$ and $R^6$ are each hydrogen or $C_1$–$C_8$–alkyl, by reacting aromatic compounds of the general formula II

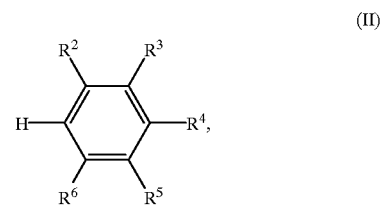

(II)

where $R^2$, $R^3$, $R^4$, $R^5$ and $R^6$ have the abovementioned meanings, with styrenes of the general formula III

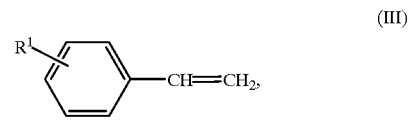

(III)

where $R^1$ has the abovementioned meanings, at from −20 to 300° C. under from 1 to 100 bar in the presence of heterogeneous catalysts, wherein beta-zeolites or mordenites are used as heterogeneous catalysts.

11 Claims, No Drawings

PREPARATION OF DIARYLETHANES

The present invention relates to a process for preparing diarylethanes by reacting aromatic compounds with styrenes in the presence of a beta-zeolite or of a mordenite as heterogeneous catalyst.

The preparation of diphenylethane by reacting aromatic compounds with styrene (derivatives) is described in JP63-238028 (1988) using Y-zeolites, in Polymer Journal, 12(1980) 407 using Nafion, Amberlyst 15 or $CF_3SO_3H$, and in EP-A-421 340 using L-zeolites. The described syntheses provide useful yields only with the introduction of alkylated aromatic compounds but still leave something to be desired. When benzene was used as aromatic compound, styrene oligomers were the main products.

It is an object of the present invention to remedy the abovementioned disadvantages.

We have found that this object is achieved by a novel and improved process for preparing diarylethanes of the general formula I

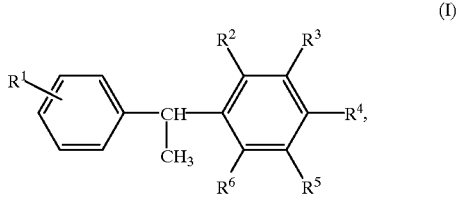

where $R^1$, $R^2$, $R^3$, $R^4$, $R^5$ and $R^6$ are each hydrogen or $C_1$–$C_8$–alkyl, by reacting aromatic compounds of the general formula II

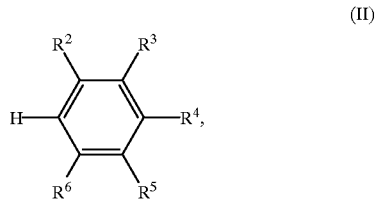

where $R^2$, $R^3$, $R^4$, $R^5$ and $R^6$ have the abovementioned meanings, with styrenes of the general formula III

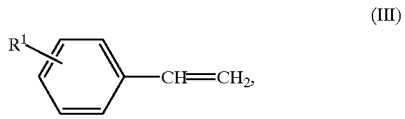

where $R^1$ has the abovementioned meanings, at from −20 to 300° C. under from 1 to 100 bar in the presence of heterogeneous catalysts, wherein beta-zeolites or mordenites are used as heterogeneous catalysts.

The process according to the invention can be carried out in the following way:

The aromatic compounds II can be reacted with the styrenes III batchwise or continuously at from −20 to 300° C., preferably 80 to 250° C., particularly preferably 80 to 200° C., under from 1 to 100 bar, preferably 1 to 30 bar, particularly preferably under atmospheric pressure, in the presence of a heterogeneous catalyst, preferably in liquid phase.

Heterogeneous catalysts which are, as a rule, suitable are strongly acidic, wide-pore zeolites such as beta-zeolites or mordenites. The catalyst can, as a rule, be either suspended in powder form in the reaction system or used as shaped bodies in a fixed bed reactor.

Beta-zeolites are disclosed, for example, in U.S. Pat. No. 3,308,069. They can be crystallized by means of tetraethylammonium hydroxide, at from 100 to 150° C., from gels with the composition $TEA_2O:SiO_2:Al_2O_3:Na_2O:H_2O$, where the $SiO_2/Al_2O_3$ ratio can be in the range from 10:1 to 200:1, and the $Na_2O/TEAOH$, $TEAOH/SiO_2$ and $H_2O/TEAOH$ ratios can be in the range from 0 to 1:1, from 0.1:1 to 1:1 and from 20:1 to 75:1, respectively. They have a wide-pore, three-dimensional pore system with 12-membered rings with diameters of 6.5×5.6 and 7.5×5.7 Å.

The reaction is, as a rule, preferably carried out under conditions which allow the styrene concentration to be low. This can take place by using dilute styrene solutions or by slowly metering the styrene into the reaction system. A particularly preferred method for batchwise preparation comprises introducing the aromatic compound together with the catalyst suspended therein into a stirred vessel and adding the styrene (or a styrene solution) dropwise during the reaction at a rate such that a stationary state between the styrene metered in and that which has reacted is set up at a low concentration level. The stationary concentration of styrene ought not to exceed 3%, preferably 0.1%, particularly preferably 0.05%. All percentages given in this application including the following examples are given by weight as conventionally determined by gas chromatography (GC) and mass spectrometry (MS).

A further particularly preferred method for continuous preparation comprises using a stirred vessel with overflow, introducing the catalyst as suspension in the particular aromatic compound into the stirred vessel and subsequently metering in a styrene/aromatic compound mixture continuously so that a low stationary styrene concentration is set up. The styrene concentration ought not to exceed 3%, preferably 0.1%, particularly preferably 0.05%. The reaction mixture emerging at the overflow can be separated from the catalyst using a settler or a filter. The catalyst can be returned, where appropriate after regeneration, to the reaction.

The diphenylethanes I can be obtained as the bottom product of a distillation.

The substituents $R^1$, $R^2$, $R^3$, $R^4$, $R^5$ and $R^6$ in the compounds I, II and III have the following meanings, and $R^1$ can be in the ortho, meta or para position:

hydrogen, $C_1$–$C_8$-alkyl, preferably $C_1$–$C_4$-alkyl such as methyl, ethyl, n-propyl, isopropyl, n-butyl, isobutyl, sec-butyl, tert-butyl, particularly preferably methyl and ethyl.

The compounds I, II and III in which all the substituents $R^1$, $R^2$, $R^3$, $R^4$, $R^5$ and $R^6$ are hydrogen, ie. 1,1-diphenylethane, benzene and styrene, are particularly preferred.

Diphenylethane is an important intermediate for preparing diphenylethene, which is used as comonomer for preparing plastics. Diphenylethene can be obtained in good yields from diphenylethane by catalytic dehydrogenation.

EXAMPLES

A gas chromatograph with a capillary column (DB5, 0.1 μm) 30 m long was used for analysis in the following experiments. (Temperature program: 5 minutes at 60° C., 10° C./minute up to 300° C., 15 minutes at the final temperature). Quantification took place using toluene as internal standard.

The three dimers which were produced (identified by GC/MS) were counted together in the following table. Their calibration factors were set equal to that for diphenylethane. The calibration factors for benzene (not listed), styrene and diphenylethane were determined using a series of concentrations with toluene as internal standard.

EXAMPLE 1

5 g of β-zeolite and 80 g of benzene were introduced into a 250 ml three-neck flask with reflux condenser, thermometer and dropping funnel and heated to reflux. Subsequently a mixture of 10 g of styrene and 10 g of benzene was added dropwise over the course of 2 hours.

The reaction mixture was then analyzed by GC.

The product contained 15.6% diphenylethane, which corresponds to a yield of 89.3%. (2.06% dimers, 0.02% trimer).

EXAMPLES 2 to 6

(dependence on concentration)

1 g of β-zeolite and 10 ml of styrene/benzene solution were stirred in a 50 ml pressure-resistant glass vessel at 30° C. for 5 h. The reaction product was then analyzed by GC.

| | | Product composition | | | |
|---|---|---|---|---|---|
| Example No. | Styrene conc. in benzene [%] | Styrene [%] | Diphenyl-ethane [%] | Dimers [%] | Trimers [%] | Yield [%] |
| 2 | 1 | 0 | 1.37 | 0.11 | 0 | 78.3 |
| 3 | 2.5 | 0 | 1.78 | 0.84 | 0 | 40.7 |
| 4 | 5 | 0 | 1.96 | 2.27 | 0.1 | 22.4 |
| 5 | 10 | 0 | 1.77 | 4.85 | 0.2 | 10.4 |
| 6 | 20 | 0 | 1.56 | 9.03 | 0.3 | 4.5 |

EXAMPLES 7 to 10

(dependence on temperature)

1 g of β-zeolite and 10 ml of a solution of 10% styrene in 90% benzene were stirred at temperature T (see table) for 5 h in a 50 ml pressure-resistant glass vessel with manometer, stirrer bar and pressure-release valve. The reaction product was then analyzed by GC.

| | | Product composition | | | |
|---|---|---|---|---|---|
| Example No. | Temperature T [° C.] | Styrene [%] | Diphenyl-ethane [%] | Dimers [%] | Trimers [%] | Yield [%] |
| 7 | 0 | 0 | 1.7 | 4.81 | 0.3 | 9.7 |
| 8 | 30 | 0 | 1.77 | 4.85 | 0.2 | 10.1 |
| 9 | 50 | 0 | 1.86 | 4.63 | 0.3 | 10.6 |
| 10 | 100 | 0 | 1.59 | 5.37 | 0.1 | 9.1 |

EXAMPLES 11 to 14

(zeolite catalysts)

1 g of zeolite and 10 ml of a solution of 10% styrene in 90% benzene were stirred at 30° C. for 5 h in a 50 ml glass flask. The reaction product was then analyzed by GC.

| | | Product composition | | | |
|---|---|---|---|---|---|
| Example No. | Catalyst | Styrene [%] | Diphenyl-ethane [%] | Dimers [%] | Trimers [%] | Yield [%] |
| 11 | ZSM-5 | 2.26 | 0 | 2.42 | 0.05 | 0 |
| 12 | L-zeolite | 9.13 | 0 | 0 | 0 | 0 |
| 13 | β-zeolite | 0 | 1.77 | 4.85 | 0.2 | 10.1 |
| 14 | mordenite | 0 | 1.59 | 3.27 | 0.1 | 6.1 |

EXAMPLES 15 to 17

(dependence on temperature in a semibatch process)

5 g of β-zeolite and 80 g of benzene were introduced into a 250 ml three-neck flask with reflux condenser, thermometer and dropping funnel and stirred at temperature T (see table). Subsequently a mixture of 10 g of styrene and 10 g of benzene was added dropwise over the course of one hour.

The reaction mixture was then analyzed by GC.

| | | Product composition | | | |
|---|---|---|---|---|---|
| Example No. | Temperature T [° C.] | Styrene [%] | Diphenyl-ethane [%] | Dimers [%] | Trimers [%] | Yield [%] |
| 15 | 30 | 1.03 | 2.4 | 5.07 | 0.05 | 13.7 |
| 16 | 50 | 2.37 | 1.92 | 4.48 | 0.02 | 11.0 |
| 17 | 80 | 0 | 13.81 | 3.61 | 0.26 | 78.9 |

EXAMPLES 18 to 20

(amount of catalyst)

X g of β-zeolite (see table) and 80 g of benzene were introduced into a 250 ml three-neck flask with reflux condenser, thermometer and dropping funnel and heated to reflux. Subsequently a mixture of 10 g of styrene and 10 g of benzene was added dropwise over the course of one hour.

The reaction mixture was then analyzed by GC.

| | | Product composition | | | |
|---|---|---|---|---|---|
| Example | Amount of | Styrene [%] | Diphenyl-ethane [%] | Dimers [%] | Trimers [%] | Yield [%] |
| 18 | 0.1 | 9.33 | 0.07 | 1.18 | 0 | 1.3 |
| 19 | 1.0 | 0 | 6.7 | 7.4 | 0.14 | 38.3 |
| 20 | 5.0 | 0 | 13.81 | 3.61 | 0.26 | 78.9 |

EXAMPLE 21

(maximum concentration)

5 g of β-zeolite and 50 g of benzene were introduced into a 250 ml three-neck flask with reflux condenser, thermometer and dropping funnel and heated to reflux. Subsequently 50 g of styrene were added dropwise over the course of 3 hours.

The reaction mixture was analyzed every 60 minutes.

| Product composition | | | | |
|---|---|---|---|---|
| Reaction time [min] | Styrene [%] | Diphenyl-ethane [%] | Dimers [%] | Trimers [%] | Yield [%] |
| 60 | 0 | 7.86 | 1.98 | 0 | 17.9 |
| 120 | 0 | 19.72 | 8.77 | 0.3 | 23.6 |
| 180 | 0.56 | 17.96 | 23.72 | 0.66 | 20.5 |

EXAMPLES 22 to 24

(continuous procedure)

10 g β-zeolite (as 1 mm pellets with 10% Pural) were packed into a tubular reactor with an internal diameter of 8 mm and a length of 1 m. The temperature of the tubular reactor was adjusted (40° C. and 75° C. in a hot-air oven, 8° C. in a cooled oil bath), and a solution of 3% styrene in 97% benzene was continuously passed through. The discharged product was analyzed at regular intervals.

| | | Product composition | | | | |
|---|---|---|---|---|---|---|
| Example No. | Temperature | Time [h] | Styrene [%] | Diphenyl-ethane [%] | Dimers [%] | Trimers [%] | Yield [%] |
| 22 | 8 | 7 | 0 | 1.52 | 1.08 | 0.07 | 28.9 |
|    | 8 | 54 | 0 | 0.72 | 1.98 | 0.06 | 13.7 |
|    | 8 | 102 | 0 | 0.48 | 1.61 | 0 | 9.1 |
| 23 | 40 | 5 | 0 | 1.1 | 1.82 | 0 | 20.9 |
|    | 40 | 42 | 0 | 0.6 | 1.28 | 0 | 11.4 |
|    | 40 | 100 | 0 | 0.2 | 1.9 | 0 | 3.8 |
| 24 | 75 | 13 | 0 | 1.05 | 1.9 | 0 | 20 |
|    | 75 | 42 | 0 | 0.61 | 1.34 | 0 | 11.6 |
|    | 75 | 108 | 0 | 0.19 | 1.02 | 0 | 3.6 |

EXAMPLE 25

(reactive distillation)

A fractionation head and, on top of this, a reflux condenser are fitted to a three-neck flask. The fractionation head is packed with 28.5 g (70 ml) of β-zeolite pellets (1 mm). A solution of 20% styrene in benzene (20 g of styrene and 80 g of benzene) is introduced into the three-neck flask and refluxed for 3 h. The composition of the bottom product was analyzed every 30 minutes.

| Product composition | | | | |
|---|---|---|---|---|
| Reaction time [min] | Styrene [%] | Diphenyl-ethane [%] | Dimers [%] | Trimers [%] |
| 30 | 28.1 | 1.35 | 0.84 | 0 |
| 60 | 11.8 | 15.0 | 8.0 | 0.2 |
| 90 | 8.9 | 17.58 | 10.7 | 0.3 |
| 120 | 6.9 | 20.42 | 13.4 | 0.34 |
| 150 | 4.5 | 25.26 | 17.1 | 0.45 |
| 180 | 2.84 | 27.99 | 19.57 | 0.54 |

We claim:

1. A process for the preparation of diarylethanes of the formula

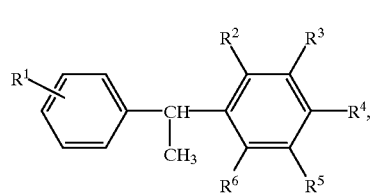

where $R^1$, $R^2$, $R^3$, $R^4$, $R^5$ and $R^6$ are each hydrogen or $C_1$–$C_8$-alkyl, which comprises reacting a mixture of an aromatic compound of the formula

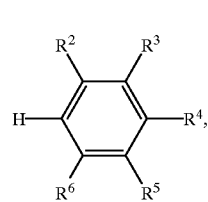

where $R^2$, $R^3$, $R^4$, $R^5$ and $R^6$ have the abovementioned meanings, with a styrene of the formula

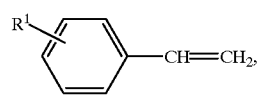

where $R^1$ has the abovementioned meanings, at a temperature of from −20 to 300° C. and under a pressure of from 1 to 100 bar in contact with a heterogenous catalyst selected from the group consisting of beta-zeolites and mordenites.

2. A process for preparing diarylethanes I as claimed in claim 1, wherein $R^1$, $R^2$, $R^3$, $R^4$, $R^5$ and $R^6$ are each hydrogen.

3. A process for preparing diarylethanes I as claimed in claim 1, wherein the reaction is carried out at from 80 to 250° C.

4. A process for preparing diarylethanes I as claimed in claim 1, wherein the reaction is carried out at from 80 to 200° C.

5. A process for preparing diarylethanes I as claimed in claim 1, wherein the reaction is carried out under from 1 to 30 bar.

6. A process for preparing diarylethanes I as claimed in claim 1 wherein the reaction is carried out under atmospheric pressure.

7. A process as claimed in claim 1, wherein the reaction is carried out by maintaining the styrene concentration in the aromatic reaction mixture at a value which does not exceed 3%.

8. A process as claimed in claim 7, wherein said styrene concentration is maintained at a value which does not exceed 0.1 %.

9. A process as claimed in claim 7, wherein said styrene concentration is maintained at a value which does not exceed 0.05%.

10. A process as claimed in claim 7, wherein benzene is the reactant II which is converted to 1,1-diphenylethane as the product I by reaction with styrene as the reactant III which is introduced into the reaction mixture at a rate sufficient to maintain its concentration below a maximum value of from 0.05 to 3%.

11. A process as claimed in claim 1, wherein the styrene reactant III admixed with the aromatic reactant II is continuously metered into a stirred suspension of the catalyst in an overflow vessel at a rate such that the concentration of said styrene III does not exceed a value of from 0.05 to 3%.

* * * * *